US012336810B2

(12) United States Patent
Riviere et al.

(10) Patent No.: US 12,336,810 B2
(45) Date of Patent: Jun. 24, 2025

(54) DETECTION OF A CHEMICAL SPECIES IN THE SWEAT OF A SUBJECT

(71) Applicant: NOPTRACK, Castres (FR)

(72) Inventors: Philippe Riviere, Toulouse (FR); Christian Amatore, Paris (FR); Gilles Favre, Cugnaux (FR); Marc Labrunee, Toulouse (FR); Frederic Daumas, Pinsaguel (FR)

(73) Assignee: NOPTRACK, Castres (FR)

( * ) Notice: Subject to any disclaimer, the term of this patent is extended or adjusted under 35 U.S.C. 154(b) by 637 days.

(21) Appl. No.: 17/778,258

(22) PCT Filed: Nov. 24, 2020

(86) PCT No.: PCT/EP2020/083210
§ 371 (c)(1),
(2) Date: May 19, 2022

(87) PCT Pub. No.: WO2021/105122
PCT Pub. Date: Jun. 3, 2021

(65) Prior Publication Data
US 2023/0337945 A1 Oct. 26, 2023

(30) Foreign Application Priority Data
Nov. 28, 2019 (FR) ...................................... 1913400

(51) Int. Cl.
*A61B 5/145* (2006.01)
*A61B 5/00* (2006.01)
(Continued)

(52) U.S. Cl.
CPC ........ *A61B 5/14517* (2013.01); *A61B 5/0004* (2013.01); *A61B 5/02055* (2013.01);
(Continued)

(58) Field of Classification Search
CPC .............. A61B 5/14517; A61B 5/0004; A61B 5/02055; A61B 5/14546; A61B 5/1477;
(Continued)

(56) References Cited

U.S. PATENT DOCUMENTS

2006/0079740 A1  4/2006  Silver et al.
2007/0225614 A1  9/2007  Naghavi et al.
(Continued)

FOREIGN PATENT DOCUMENTS

CN    109060923 A    12/2018
EP    0384090 A1    8/1990
(Continued)

OTHER PUBLICATIONS

Chinese Office Action for Patent Application No. 202080082726.8, mailed on Aug. 29, 2024 with machine translation.
(Continued)

*Primary Examiner* — Eric F Winakur
*Assistant Examiner* — Noah M Healy
(74) *Attorney, Agent, or Firm* — Notaro, Michalos & Zaccaria P.C.

(57) ABSTRACT

A detection apparatus detects at least one chemical species in the sweat of a human or animal subject, the at least one chemical species being selected from the group consisting of nitrogen oxide NO, nitrite ion NO2− and hydrogen peroxide H2O2. The apparatus has a collection element that is intended to be positioned in an investigation zone of an epidermis of the subject, and a detection device has at least one fluid circuit that is coupled to the collection element in order to direct at least one flow of sweat from the investigation zone and an electrochemical sensor having electrodes that are arranged in the fluid circuit, the electrochemical sensor being configured to produce a signal that represents a concentration of the at least one chemical species in the
(Continued)

flow of sweat and a signal that represents a flow speed of the flow of sweat.

22 Claims, 6 Drawing Sheets

(51) Int. Cl.
    *A61B 5/0205*         (2006.01)
    *A61B 5/1477*         (2006.01)
    *A61B 10/00*          (2006.01)
    *A61B 5/11*            (2006.01)

(52) U.S. Cl.
    CPC ........ *A61B 5/14546* (2013.01); *A61B 5/1477* (2013.01); *A61B 10/0064* (2013.01); *A61B 5/1118* (2013.01)

(58) Field of Classification Search
    CPC ..... A61B 10/0064; A61B 5/4266; A61B 5/01; A61B 5/1468; A61B 5/746; A61B 2562/0219; A61B 5/7275; A61B 5/0205; A61B 5/02438; A61B 5/6833; G16H 50/20
See application file for complete search history.

(56) References Cited

U.S. PATENT DOCUMENTS

| | | | |
|---|---|---|---|
| 2015/0335288 A1* | 11/2015 | Toth | A61B 5/388 600/391 |
| 2017/0184564 A1 | 6/2017 | Liu et al. | |
| 2018/0064377 A1* | 3/2018 | Rogers | B01L 3/5027 |
| 2018/0070869 A1 | 3/2018 | Onescu et al. | |
| 2018/0217087 A1 | 8/2018 | Swain et al. | |
| 2019/0008448 A1 | 1/2019 | Begtrup et al. | |
| 2019/0110722 A1 | 4/2019 | Ionescu et al. | |

FOREIGN PATENT DOCUMENTS

| | | |
|---|---|---|
| JP | H08220054 A | 8/1996 |
| JP | 2010210328 A | 9/2010 |
| WO | 9808480 A2 | 3/1998 |
| WO | WO2008041984 A1 | 4/2008 |
| WO | 2016061362 A2 | 4/2016 |
| WO | WO2019143611 A1 | 7/2019 |
| WO | 2019170776 A1 | 9/2019 |
| WO | 2019210240 A1 | 10/2019 |
| WO | 2019229380 A1 | 12/2019 |

OTHER PUBLICATIONS

Japanese Office Action for Patent Application No. 2022-531479, mailed on Jul. 30, 2024 with machine translation.
Kenny Walter, "Novel Wearable Sensor Monitors Health Through Sweat Using Nanotech", Research & Development World, Apr. 26, 2019 (Apr. 26, 2019), https://www.rdworldonline.com/novel-wearable-sensor-monitors-health-through-sweat-using-nanotech/ , retrieved May 19, 2022.
Richard Weller et al., "Nitric Oxide Is Generated on the Skin Surface by Reduction of Sweat Nitrate" Journal of Investigative Dermatology, vol. 107, No. 3, Sep. 1, 1996 (Sep. 1, 1996), pp. 327-331 DOI: 10.1 1111/1523-1 747.epl2363167, retrieved May 19, 2022.
Bruch-Gerharz D et al., "Nitric oxide in human skin: current status and future prospects" Journal of Investigative Dermatology, Elsevier, NL, vol. 110, No. 1, Jan. 1, 1998 (Jan. 1, 1998), pp. 1-7 DOI: 10.1046/J.1523-1747.1998.00084.X ISSN: 0022-202X, XP002254968, retrieved May 19, 2022.
Byeong Wan An et al., "Smart Sensor Systems for Wearable Electronic Devices" Polymers, vol. 9, No. 12, Jul. 25, 2017 (Jul. 25, 2017), p. 303 DOI: 10.3390/polym9080303 XP055526164, retrieved May 19, 2022.
Salzitsa Anastasova et al., "A wearable multisensing patch for continuous sweat monitoring" Biosensors and Bioelectronics, Amsterdam, NL, vol. 93, Jul. 1, 2017 (Jul. 1, 2017), pp. 139-145 DOI: 10.1016/j.bios.2016.09.038 ISSN: 0956-5663, XP055482880, retrieved May 19, 2022.
A. Abellan-Llobregat et al., "A stretchable and screen-printed electrochemical sensor for glucose determination in human perspiration" Biosensors and Bioelectronics, Amsterdam, NL, vol. 91, May 1, 2017 (May 1, 2017). pp. 885-891DOI: 10.1016/j.bios.2017.01.058ISSN: 0956-5663, XP055738168, retrieved May 19, 2022.
Jungil Choi et al., "Skin-interfaced systems for sweat collection and analytics" Science, vol. 4, No. 2, Feb. 16, 2018 (Feb. 16, 2018), p. eaar3921 DOI: 10.1 126/sciadv.aar3921 ISSN: 0036-8075, XP055526287, retrieved May 19, 2022.
Yejin Ha et al., "Measurements of Location-Dependent Nitric Oxide Levels on Skin Surface in relation to Acupuncture Point", Evidence-Based Complementary and Alternative Medicine, vol. 2012, Jan. 1, 2012 (Jan. 1, 2012), pp. 1-7 DOI: 10.1155/2012/781460 ISSN: 1 741-427X, XP055524807, retrieved May 19, 2022.
Albert Maarek et al., "Detection of neuropathy using a sudomotor test in type 2 diabetes" Degenerative Neurological and Neuromuscular Disease, Jan. 9, 2015 (Jan. 9, 2015), p. 1 DOI: 10.2147/DNND.S75857 ISSN: 1179-9900, XP055525495, retrieved May 19, 2022.
Youngmi Lee et al., "Improved Planar Amperometric Nitric Oxide Sensor Based on Platinized Platinum Anode. 1. Experimental Results and Theory When Applied for Monitoring NO Release from Diazeniumdiolate-Doped Polymeric Films—Analytical Chemistry (ACS Publications)" Jan. 1, 2004 (Jan. 1, 2004). Retrieved from the Internet: https://pubs.acs.org/doi/10.1021/ac035064h, retrieved May 19, 2022.
Ma et al., "Evidence of enhanced non-enzymatic generation of nitric oxide on the skin surface of acupuncture points: An innovative approach in humans" Nitric Oxide: Biology and Chemistry, Academic Press, Amsterdam, NL, vol. 17, No. 2, Aug. 18, 2007 (Aug. 18, 2007), pp. 60-68 DOI: 10.1016/J.NIOX.2007.05.004 ISSN: 1089-8603, XP022207173, retrieved May 19, 2022.
Mallika Bariy A et al., "Wearable sweat sensors" Nature Electronics, vol. 1, No. 3, Mar. 1, 2018 (Mar. 1, 2018), pp. 160-171 DOI: 10.1038/s41928-018-0043-y ISSN: 2520-1131, XP055525597, retrieved May 19, 2022.
Johne Lewis et al., "New method of sudomotor function measurement to detect microvascular disease and sweat gland nerve or unmyelinated C fiber dysfunction in adults with retinopathy" Journal of Diabetes & Metabolic Disorders, Biomed Central Ltd, London, UK, vol. 16, No. 1, Jun. 12, 2017 (Jun. 12, 2017), pp. 1-10 DOI: 10.1 186/S40200-017-0307-5 XP021245874, retrieved May 19, 2022.
Yejin Ha et al., "Insertable NO/CO Microsensors Recording Gaseous Vasomodulators Reflecting Differential Neuronal Activation Level with Respect to Seizure Focus" ACS Chemical Neuroscience, US, vol. 8, No. 9, Jul. 5, 2017 (Jul. 5, 2017), pp. 1853-1858 DOI: 10.1021/acschemneuro.7b00141 ISSN: 1948-7193, XP055524923, retrieved May 19, 2022.
Kichang Lee et al., "Role of nitric oxide in methacholine-induced sweating and vasodilation in human skin" Journal of Applied Physiology, United States, Apr. 1, 2006 (Apr. 1, 2006), pp. 1355-1360, Retrieved from the Internet: https://pdfs.semanticscholar.org/c834/lf4a660265al 2e6e0bf87ba563ab9b9felce.pdf DOI: 10.1 152/japplphysiol.00122.2005 XP055525486, retrieved May 19, 2022.
Vincenzo F. Curto et al., "Real-time sweat pH monitoring based on a wearable chemical barcode micro-fluidic platform incorporating ionic liquids" Sensors and Actuators B: Chemical: International Journal Devoted to Research and Development of Physical and Chemical Transducers, NL, vol. 171-172, Aug. 1, 2012 (Aug. 1, 2012), pp. 1327-1334 DOI: 10.1016/j.snb.2012.06.048 ISSN: 0925-4005, XP055451404, retrieved May 19, 2022.
Hnin Yin Yin Nyein et al., "A Wearable Microfluidic Sensing Patch for Dynamic Sweat Secretion Analysis" ACS Sensors, vol. 3, No. 5, May 9, 2018 (May 9, 2018), pp. 944-952 DOI: 10.1021/acssensors.7b00961 ISSN: 2379-3694, XP055525587, retrieved May 19, 2022.
Kramer Ry an Met al., "Analytical determination and detection of individual odor signatures" Sensing Technologies for Global Health, Military Medicine, Disaster Response, and Environmental Moni- (56) References Cited

OTHER PUBLICATIONS toring II; and Biometric Technology for Human Identification IX, SPIE, 1000 20th St. Bellingham WA 98225-6705 USA, vol. 8371, No. 1, May 11, 2012 (May 11, 2012), pp. 1-14 DOI: 10.1117/12. 919921, retrieved May 19, 2022.

Yejin Ha et al., "Amperometric Microsensors Monitoring Glutamate-Evoked In Situ Responses of Nitric Oxide and Carbon Monoxide from Live Human Neuroblastoma Cells" Sensors, vol. 17, No. 7, Jul. 19, 2017 (Jul. 19, 2017), p. 1661 DOI: 10.3390/sl 7071661 XP055524813, retrieved May 19, 2022.

GF Clough et al., "Measurement of nitric oxide concentration in human skin in vivo using dermal microdialysis" Experimental Physiology, GB, vol. 83, No. 3, May 1, 1998 (May 1, 1998), pp. 431-434DOI: 10.1 1 13/expphysiol.1998.sp004126ISSN: 0958-0670, XP055526121, retrieved May 19, 2022.

Luo Xiaojin et al., "A Wearable Amperometric Biosensor on a Cotton Fabric for Lactate" IEEE Electron Device Letters, IEEE Service Center, New York, NY, US, vol. 39, No. 1, Jan. 1, 2018 (Jan. 1, 2018), pp. 123-126, [retrieved on Dec. 26, 2017] DOI: 10.1109/ LED.2017.2777474 ISSN: 0741-3106, XP011675011, retrieved May 19, 2022.

International Search Report for corresponding PCT application No. PCT/EP2020/083210, mailed Jan. 29, 2021.

\* cited by examiner

DETECTION OF A CHEMICAL SPECIES IN THE SWEAT OF A SUBJECT

TECHNICAL FIELD

The invention relates to methods and apparatus for detecting at least one chemical species in the sweat of a human or animal subject, in particular one or more chemical species selected from the group consisting of nitric oxide (NO), the nitrite ion ($NO_2^-$) and hydrogen peroxide ($H_2O_2$).

TECHNICAL BACKGROUND

Nitric oxide is a gas that constitutes an intercellular messenger. It is an important cardiovascular messenger for stress by mechanotransduction. In particular, it is released in order to stimulate vasodilation of the vascular system during muscular exertion. Variations in the flow produced in the blood and therefore in the liquids in equilibrium with the blood, for example sweat, therefore constitute a particularly pertinent indicator of the cardiovascular capacity of a patient to adapt to the muscle power demanded during exertion tests.

In the case of a cardiovascular disease, extant devices and tools for prevention and prediction are either limited to an indirect measurement of nitric oxide in the patient while resting, or limited to a direct measurement separated by several hours with respect to an observation of a pathological problem. In all cases, the measurements can only be carried out in a clinical environment.

SUMMARY

Certain aspects of the invention are based on the concept that the quantitative measurement of variations in the concentration of nitric oxide in sweat provides a non-invasive method for monitoring cardiovascular capacity during preventive monitoring or in order to make a diagnosis.

Certain aspects of the invention are based on the observation that, in the presence of dioxygen, nitric oxide reacts to produce a nitrite ion ($NO2^-$) via a reaction with an overall stoichiometry of 1:1. In other words, while the variations in the concentration of nitric oxide represent the current state of responses of the cardiovascular system to a given exertion, variations in the concentration of the nitrite ion constitute a temporal record of these responses.

Certain aspects of the invention are based on the concept that the variations in the concentrations of nitric oxide and of the nitrite ion can be detected and quantified in a manner which is coupled with an integrated electrochemical device.

Certain aspects of the invention are based on the observation that nitric oxide is produced by specialized enzymes (NO synthases) from the degradation of intracellular L-arginine in the presence of dioxygen ($O_2$) and a source of electrons. When the availability of L-arginine reduces because of high consumption (for example following prolonged exertion) or a chronic deficiency, the NO synthases continue to react with oxygen by restricting themselves to reducing dioxygen to the superoxide ion ($O_2^-$). This ion spontaneously and very rapidly transforms into hydrogen peroxide ($H_2O_2$) via a reaction with an overall stoichiometry of 2:1. Certain aspects of the invention are based on the concept that the presence of detectable concentrations of hydrogen peroxide in blood, and therefore in sweat, provides an indicator representing a level of distress in the cardiovascular system. In addition, in the presence of metal salts, hydrogen peroxide decomposes into highly toxic radical species ($HO^*$, $HO_2^*$ etc.) that are capable of causing a great deal of damage to cells of the cardiovascular system, including those of the heart. Certain aspects of the invention are based on the concept that the detection of hydrogen peroxide production at the same time as the detection of nitric oxide production and/or nitrite ion production is pertinent to the assessment of the cardiovascular capacities of a patient.

Certain aspects of the invention are based on the concept of detecting the three chemical species mentioned above coupled with an integrated electrochemical device.

Certain aspects of the invention are based on the observation that the physiological system of a subject is dynamic because the volumetric flow of sweat can vary in order to adjust the ability to eliminate heat produced as a function of the delivered muscle power. The exchange flows for each chemical species at the blood-sweat interfaces can vary as a function of exertion by the subject. Certain aspects of the invention are based on the idea of detecting, in a quantitative and dynamic manner, the production of one or more of the aforementioned chemical species by the cardiovascular system, for example during an exertion test or medical monitoring of a subject.

To this end, in accordance with one embodiment, the invention provides a detection apparatus for detecting at least one chemical species in a biological liquid, for example sweat, of a subject, for example human or animal, said at least one chemical species being selected from the group consisting of nitric oxide NO, the nitrite ion $NO_2^-$ and hydrogen peroxide $H_2O_2$ and preferably including nitric oxide NO, said apparatus comprising:

- a collecting element intended to be placed on an investigation zone of a subject's epidermis,
- and a detection device comprising at least one fluidic circuit coupled to the collecting element in order to conduct at least one flow of sweat originating from the investigation zone, and at least one electrochemical sensor comprising electrodes disposed in the fluidic circuit, the electrochemical sensor being configured to produce a signal that is representative of a concentration of said at least one chemical species in the flow of sweat.

The term "a chemical species in a biological liquid" means that the chemical species, in particular nitric oxide, is dissolved in the biological liquid.

The term "an epidermis" means the superficial plant tissue forming a protective layer for the aerial parts of a plant or the superficial layer of the skin in humans and animals. As an example, the biological liquid is an exudate in plants or sweat in humans and animals.

In accordance with some embodiments, an apparatus of this type may comprise one or more of the following features.

In accordance with one embodiment, the or each or at least one said electrochemical sensor is configured to additionally produce a signal that is representative of a flow velocity of the flow of sweat or a volumetric flow of sweat.

In accordance with one embodiment, the detection device is configured to produce a signal that is representative of an instantaneous production of said at least one chemical species in the investigation zone on the basis of a signal that is representative of the concentration of said at least one chemical species and of a signal that is representative of the flow velocity of the flow of sweat.

The term "instantaneous production" means a measurement taken over a very short duration compared with the characteristic time for the variation in the physiological response of the subject. This characteristic time is typically of the order of one to a few minutes for a human subject.

In accordance with one embodiment, the or each or at least one said electrochemical sensor comprises at least one working electrode and a counter-electrode disposed in the fluidic circuit, the electrochemical sensor being configured to produce a signal that is representative of the concentration of the at least one chemical species by an electrical measurement, in particular amperometric, between the at least one working electrode and the counter-electrode.

In accordance with one embodiment, the or each or at least one said electrochemical sensor comprises an upstream working electrode and a downstream working electrode spaced apart in the fluidic circuit in a direction of flow of the flow of sweat, the electrochemical sensor being configured to produce the signal that is representative of the flow velocity by measuring a delay between a variation in current or potential in the upstream working electrode and a variation in current or potential in the downstream working electrode.

In accordance with one embodiment, the distance L separating the upstream working electrode and the downstream working electrode is comprised between 0.05 mm and 1 cm.

In accordance with one embodiment, the or at least one said electrochemical sensor is configured to polarize the electrodes to an electrical potential for the oxidation of nitric oxide and the detection device comprises a filter configured to filter the flow of sweat reaching the electrochemical sensor in order to eliminate hydrogen peroxide in particular.

A filter of this type may be produced in different manners, for example with a membrane produced from polytetrafluoroethylene (PTFE) or a membrane of the eugenol type, which may be disposed in the fluidic circuit. In accordance with one embodiment, the filter comprises a layer of eugenol (4-allyl-2methoxyphenol) deposited on at least one electrode of the electrochemical sensor.

This configuration based on a detection electrode modified with this type of filter that is specifically for the measurement of NO directly produces a signal that is representative of the concentration of nitric oxide NO on the basis of an amperometric measurement signal.

In accordance with the embodiments described below, the detecting device is produced in a manner such that it can simultaneously or sequentially detect two or three of the aforementioned chemical species with one or more electrochemical sensors.

In accordance with one embodiment, said at least one chemical species comprises nitric oxide NO and the nitrite ion $NO_2^-$. In accordance with one embodiment, said at least one chemical species comprises nitric oxide NO and hydrogen peroxide $H_2O_2$. In accordance with one embodiment, said at least one chemical species comprises nitric oxide NO, the nitrite ion $NO_2$ and hydrogen peroxide $H_2O_2$.

In accordance with one embodiment that enables sequential detection, the or each or at least one said electrochemical sensor is configured for the sequential detection of several chemical species during a plurality of measurement steps, the electrochemical sensor being configured to polarize the electrodes to an electrical potential for the oxidation of hydrogen peroxide $H_2O_2$ during a first step and to polarize the electrodes to an electrical potential for the oxidation of nitric oxide NO during a second step, and the detection device is configured to produce a signal that is representative of a concentration of nitric oxide NO on the basis of a first amperometric measurement signal obtained during the first step and of a second amperometric measurement signal obtained during the second step.

Advantageously in this case, the or each or at least one said electrochemical sensor is configured to polarize the electrodes to an electrical potential for the oxidation of the nitrite ion $NO_2$ during a third step, and the detection device is configured to produce a signal that is representative of a concentration of the nitrite ion $NO_2$ on the basis of said first and second amperometric measurement signals and of a third amperometric measurement signal obtained during the third step.

In accordance with one embodiment, the detection device is produced in a manner such as to be capable of the sequential detection of three of the aforementioned chemical species with a single electrochemical sensor during a plurality of steps of temporal sequences of measurements. In accordance with this embodiment, during a given sequence, the electrochemical sensor is configured to polarize a platinized platinum electrode (coated with platinum black) in sequence up to the electrochemical potential for the oxidation of hydrogen peroxide $H_2O_2$ during a first temporal step of a few seconds (5 s, for example), then to that for the oxidation of nitric oxide NO during a second temporal step of the same duration, and optionally to that of the nitrite ion $NO_2$ during a third temporal step of the same duration. The detection device is configured to produce a signal that is representative of a concentration of nitric oxide NO on the basis of a first amperometric measurement signal obtained during the first step and of a second amperometric measurement signal obtained during the second step. This sequence is repeated as often as is necessary over the total duration of the exertion test. Solving a series of three equations (the currents measured sequentially on the electrode which has been polarized to each potential in one sequence) with two or three unknowns (the concentrations of $H_2O_2$, NO and nitrite $NO_2$) provides values for each of the three concentrations at the moment at which each sequence is produced on the basis of the three measurements.

In accordance with another embodiment that enables simultaneous detection, the detection device comprises:
a first fluidic circuit coupled to the collecting element in order to conduct a first flow of sweat originating from the investigation zone and a first electrochemical sensor comprising electrodes disposed in the first fluidic circuit, the first electrochemical sensor being configured to polarize the electrodes to an electrical potential for the oxidation of hydrogen peroxide $H_2O_2$, and
a second fluidic circuit coupled to the collecting element in order to conduct a second flow of sweat originating from the investigation zone and a second electrochemical sensor comprising electrodes disposed in the second fluidic circuit, the second electrochemical sensor being configured to polarize the electrodes to an electrical potential for the oxidation of nitric oxide NO,
and the detection device is configured to produce a signal that is representative of a concentration of nitric oxide NO on the basis of a first amperometric measurement signal produced by the first electrochemical sensor and of a second amperometric measurement signal produced by the second electrochemical sensor.

Advantageously in this case, the detection device additionally comprises:
a third fluidic circuit coupled to the collecting element in order to conduct a third flow of sweat originating from the investigation zone and a third electrochemical sensor comprising electrodes disposed in the third fluidic circuit, the third electrochemical sensor being configured to polarize the electrodes to an electrical potential for the oxidation of the nitrite ion $NO_2$, and the detection device is configured to produce a signal that is representative of a concentration of the nitrite ion $NO_2$ on the basis of said first and second amperometric measurement signals and of a third amperometric measurement signal produced by the third electrochemical sensor.

In accordance with this embodiment, the detection device comprises three parallel microfluidic circuits supplied in parallel via the same sweat collecting element.

In accordance with one embodiment, the detection device additionally comprises: another fluidic circuit, for example a fourth fluidic circuit, coupled to the collecting element in order to conduct another flow of sweat originating from the investigation zone, for example a fourth flow of sweat, and another electrochemical sensor, for example a fourth electrochemical sensor, comprising electrodes disposed in the fourth fluidic circuit.

In accordance with this embodiment, said other or fourth electrochemical sensor is configured to polarize the electrodes to an electrical potential for the oxidation of nitric oxide and the fourth fluidic circuit comprises a filter configured to filter the flow of sweat reaching the fourth electrochemical sensor in order to eliminate hydrogen peroxide in particular.

In accordance with one embodiment, the collecting element comprises a fibrous body in order to conduct the biological liquid from the investigation zone, in particular sweat, by capillary action. A fibrous body of this type may be a woven or nonwoven material.

In accordance with one embodiment, the apparatus additionally comprises an envelope surrounding the collecting element in a manner such as to form an impervious barrier around the investigation zone by contact with the epidermis of said subject.

Because of these features, gases, liquids and microorganisms such as bacteria or viruses situated outside the investigation zone cannot enter the investigation zone. The imperviousness of the contact between the envelope and the epidermis ensures that the chemical species that is detected originates from the biological liquid produced by the investigation zone and not from a flow from outside.

In accordance with one embodiment, the apparatus additionally comprises a wired or wireless communication device configured to transmit one or more measurement signals produced by the detection device to a post-processing device.

In accordance with one embodiment, the or each or at least one said fluidic circuit is formed in an insulating support and the electrodes of the or each least one said electrochemical sensor are constituted by metallic deposits on said insulating support. An insulating support of this type may be produced from a material selected from elastomers, for example from polydimethylsiloxane (PDMS), polyimides, epoxy resins and parylene.

In accordance with one embodiment, the metallic deposits are selected from the group consisting of silver (Ag), gold (Au), platinum (Pt) and platinum black. In accordance with one embodiment, the electrochemical sensor comprises a reference electrode produced from silver chloride (AgCl).

In an interesting embodiment, the electrodes are constituted by deposits of graphene doped with nanoparticles of silver (Ag) or gold (Au), the nanoparticles being functionalized by binders for nitric oxide, in particular guanylyl cyclase or porphyrins.

In accordance with one embodiment, the apparatus is configured to carry out and periodically transmit measurements, for example at a customizable frequency or at a frequency that is dependent on a state of activity detected by the apparatus. As an example, the apparatus may comprise a gyroscopic module and/or an accelerometer in order to detect the state of activity of the subject. Thus, it is possible to detect the state of activity of the subject during the sweat analysis, in order to facilitate an analysis of correlations between the state of activity of the subject and the production of the analyzed chemical species.

In accordance with one embodiment, the apparatus comprises a geopositioning module.

In accordance with one embodiment, the invention also provides a method for determining the production of at least one chemical species by a human or animal subject, said at least one chemical species being selected from the group consisting of nitric oxide NO, the nitrite ion $NO_2$ and hydrogen peroxide $H_2O_2$ and preferably including nitric oxide NO, the method comprising:
  selecting an investigation zone of an epidermis of said subject,
  applying an apparatus as mentioned above for a duration that is necessary for the production of the signal that is representative of a concentration of said at least one chemical species in the flow of sweat and, if appropriate, the signal that is representative of a flow velocity of the flow of sweat, and
  determining a measurement of the production of said at least one chemical species by the subject from a signal that is representative of the concentration of said at least one chemical species in the flow of sweat and if appropriate, of a signal that is representative of the flow velocity of the flow of sweat.

The measurements of the production of one or more of the aforementioned chemical species by the subject may be exploited in a variety of applications, for example in order to evaluate distress in the vascular tissues of the subject from these measurements or in order to evaluate a cardiovascular capacity of the subject from these measurements.

Other possible applications are diagnostics, medical care and monitoring diseases such as cardiovascular disease, neurodegenerative disease, pulmonary arterial hypertension, cancer, hypercholesterolemia, diabetes, systemic endothelial dysfunction, arteriosclerosis, thrombotic or ischemic disease, platelet accumulation inhibition dysfunction or leukocyte adhesion deficiency or cell proliferation dysfunction in smooth muscle fiber cells, bronchial inflammation, asthma, Alzheimer's disease.

Other possible applications are monitoring growth and/or muscular distress in an individual, for example an individual who is undergoing physical training, the prevention of injuries due to overtraining and/or enhancing the muscle performance of the subject.

BRIEF DESCRIPTION OF THE FIGURES

In order to understand the subject matter of the invention better, an embodiment as shown in the accompanying drawings will now be described below, by way of purely illustrative and non-limiting example. In the drawings.

DESCRIPTION OF EMBODIMENTS

Figure 1:
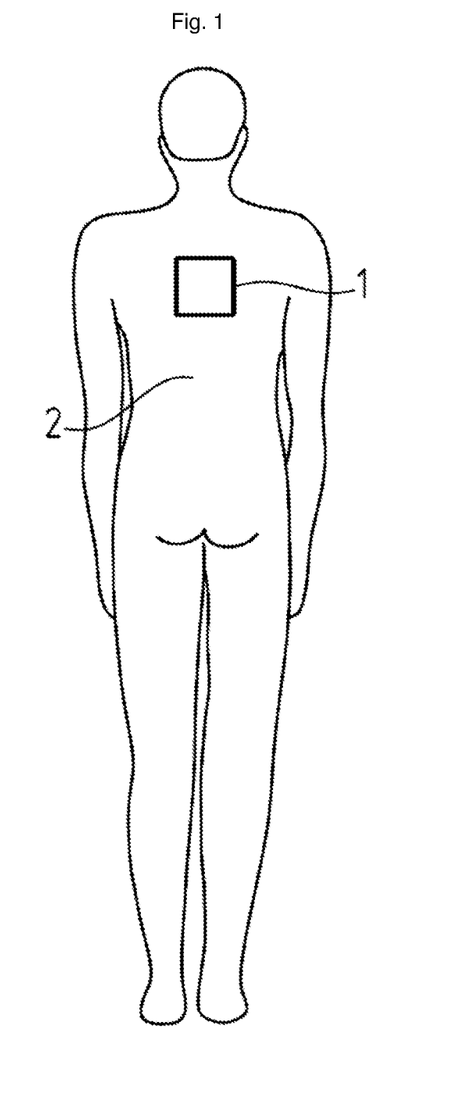
FIG. 1 represents a schematic view of the back of a subject on which an apparatus in accordance with one embodiment has been positioned.

FIG. 1 shows a detection apparatus 1 disposed on the skin of a human subject 2, for example on the back of the subject, and intended to carry out quantitative measurements of chemical species dissolved in sweat, including nitric oxide dissolved in sweat, and optionally the nitrite ion and hydrogen peroxide.

Figure 2:
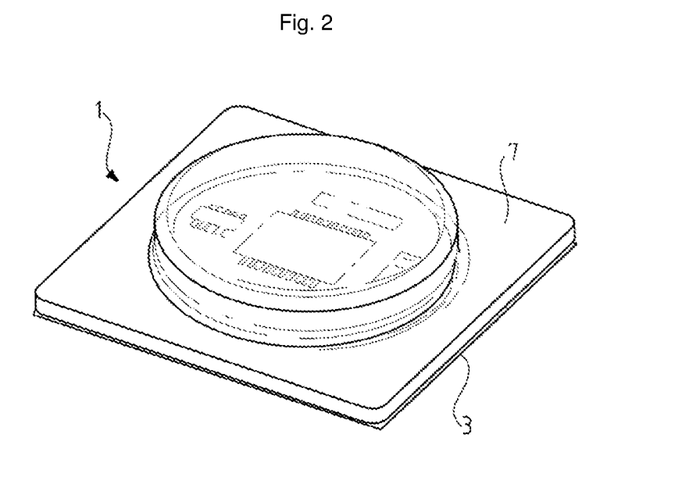
FIG. 2 is a perspective view representing a detection apparatus in accordance with one embodiment.

Referring to FIG. 2, by way of example, the detection apparatus 1 is shown in the form of a compact casing which comprises a base plate 3 made from a biocompatible flexible material, preferably self-adhesive, which can be positioned directly onto the skin of the subject, and an upper envelope 7, preferably impervious to water, for example silicone, which encloses the other components of the detection apparatus 1.

Figure 3:
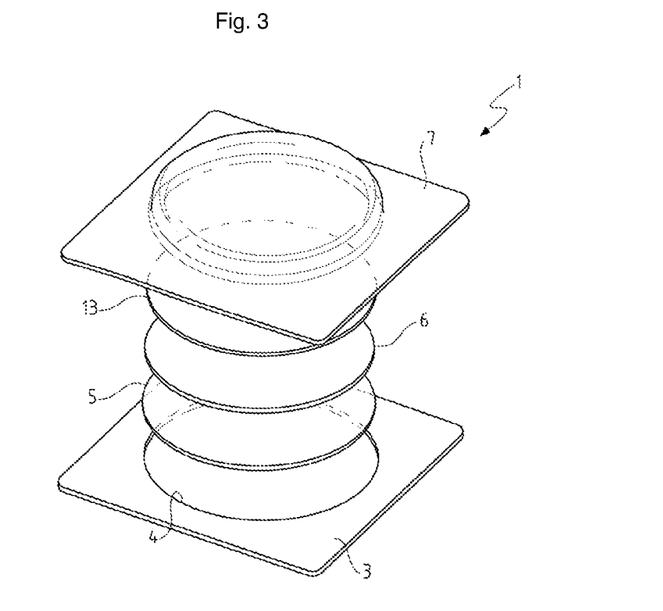
FIG. 3 represents an exploded view of the apparatus of FIG. 2.

Referring now to FIG. 3, a central portion of the base plate 3 comprises a circular recess 4 delimiting an investigation zone on the skin of the subject and which may, for example, be from a few mm to a few cm in diameter. The circular recess 4 contains a collecting element 5 which is then positioned directly onto the skin 2 of the subject when the apparatus is operating. The recess 4 may have another shape, for example an ellipse, a triangle, a rectangle, a square, a polygon or other shape.

As an example, the collecting element 5 comprises a fibrous body such as cotton or a nonwoven material. The collecting element 5 is connected to a support 6 carrying one or more fluidic circuits and one or more sensors as will be described below. The support 6 may be a rigid or flexible support, for example produced from polyimide. The collecting element 5 fulfils the functions of bringing the sweat produced in the investigation zone to the fluidic circuits of the support 5 in order to enable the detection of one or more chemical species with the aid of the sensors. To this end, the collecting element 5 may be disposed in a variety of manners.

Figure 4:
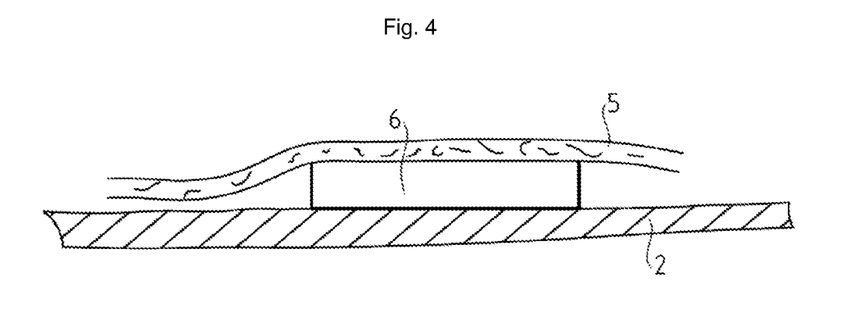
FIG. 4 is a schematic sectional view of a collecting element in accordance with a first embodiment which can be used in the apparatus of FIG. 2.

In the example of FIG. 4, the collecting element 5 has a portion in contact with the skin 2 to the side of the support 6 and a portion which will cover an upper face of the support 6. In other words, the collecting element 5 is mounted between the skin and the support 6. On the upper face of the support 6, the collecting element 5 communicates with the fluidic circuits provided with sensors.

Figure 5:
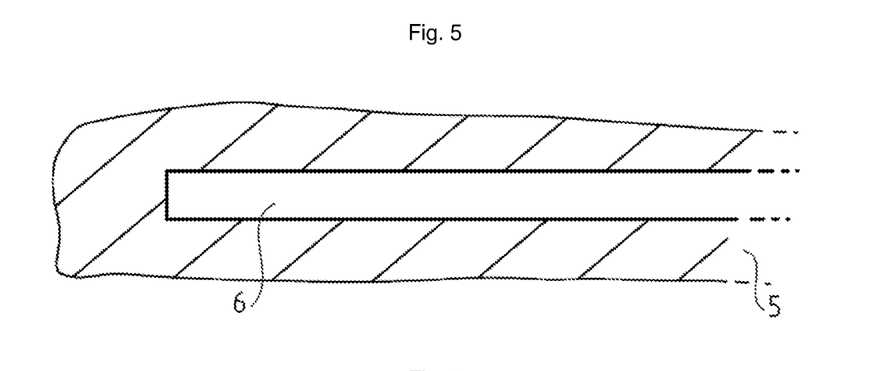
FIG. 5 is a schematic sectional view of a collecting element in accordance with a second embodiment which can be used in the apparatus of FIG. 2.

In the example of FIG. 5, the collecting element 5 will form a sandwich around the support 6. The result of this is that a portion of the collecting element 5 disposed below the support 6 is disposed against the skin. A portion of the collecting element 5 that extends the portion disposed on the skin is folded over the support 6 and will therefore cover the support 6. On the upper face of the support 6, the collecting element 5 communicates with the fluidic circuits provided with the sensors.

Figure 6:
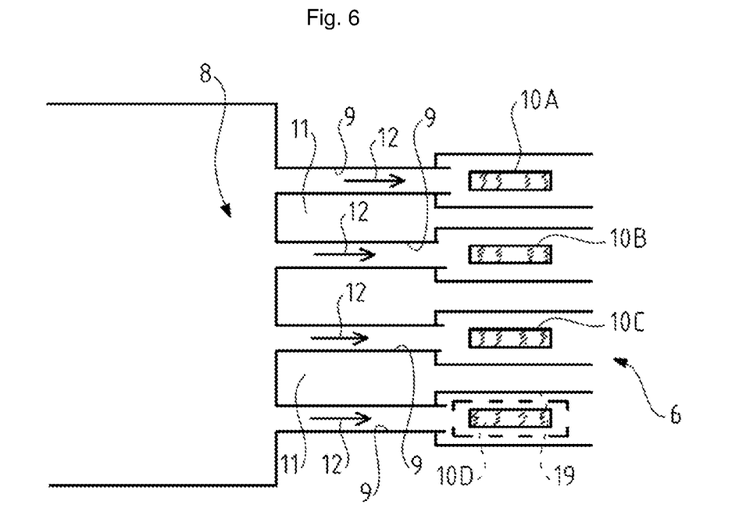
FIG. 6 is a schematic functional representation of a fluidic circuit which can be used in the apparatus of FIG. 2.

With reference to FIG. 6, the support 6 carries a microfluidic system 8 which is supplied via the collecting element 5 by capillary action. Sweat is collected by the portion of the collecting element 5 placed in contact with the skin 2 then transferred by capillary action so that it moves into the microfluidic system 8. The microfluidic system 8 may comprise one or more fluidic circuits, namely four parallel fluidic circuits 9 in the example shown. The fluidic circuits 9 are, for example, formed in the thickness of the support 6 and separated by partitions 11. The fluidic circuits 9 may therefore form separate channels in which the sweat can move independently. The number of fluidic circuits 9 may be higher or lower than that shown in the drawing.

Each fluidic circuit 9 is provided with a sensor 10A, 10B, 10C or 10D. The arrows 12 illustrate the direction of flow of the sweat in the fluidic circuits 9. Preferably, the fluidic circuits 9 discharge into a drainage reservoir which holds the analyzed fluids in order to prevent the reaction products from the electrolysis from coming into contact again with the skin of the subject.

The sensors 10A, 10B, 10C and 10D arranged in the fluidic circuits 9 for sweat analysis are preferably electrochemical sensors. The operating principle of an electrochemical sensor is to electrolyze the solution present in the fluidic circuit 9 between a working electrode and a counter-electrode. This type of sensor may be produced in a variety of manners, in particular in a miniaturized manner with dimensions of the order of a millimeter.

Several examples of embodiments of electrochemical sensors will now be described with reference to FIG. 6.

EXAMPLES

Example 1

The sensor 10A is intended to detect hydrogen peroxide. It therefore operates with a potential difference $E_{H2O2}$ equal to the oxidation potential of hydrogen peroxide. The sensor 10B is intended to detect nitric oxide. It therefore operates with a potential difference $E_{NO}$ equal to the oxidation potential of nitric oxide. The sensor 10C is intended to detect the nitrite ion. It therefore operates with a potential difference $E_{NO2-}$ equal to the oxidation potential of the nitrite ion.

The sensors 10A, 10B, 10C carry out instantaneous intensity measurements, denoted $i_{oxdn}$, of the faradic currents linked to the electrochemical oxidation of the aforementioned chemical species. The sensors 10a, 10B, 10C can therefore be used to detect and quantify the instantaneous concentration of the aforementioned chemical species.

Each of the three aforementioned chemical species can be detected by amperometric measurements with the aid of microelectrodes. They are constituted, for example, by strips of platinum covered with a thin layer, for example of micrometric dimensions, of platinum black deposited by electrochemical reduction, in an aqueous medium, of the anion of a platinum salt, $Pt(Cl)_6^{4-}$.

The three chemical species ($NO$, $NO_2^-$ and $H_2O_2$) can be distinguished by the fact that their oxidation potentials on these electrodes are clearly separated, occurring in the following order: $E_{H2O2} < E_{NO} < E_{NO2-}$. However, the faradic currents are additive. The measured current at the oxidation potential of each chemical species therefore adds to the elementary currents linked to the oxidation of this chemical species and to the oxidation of all of the chemical species which have lower oxidation potentials.

Thus, only the species $H_2O_2$ can be oxidized at the oxidation potential $E_{H2O2}$. The species $H_2O_2$ and NO can be oxidized at the oxidation potential $E_{NO}$. The three species can be oxidized at the oxidation potential $E_{NO2-}$. The currents measured by the sensors 10A to 10C, respectively denoted $i_{oxdn}(E_{H2O2})$, $i_{oxdn}(E_{NO})$ and $i_{oxdn}(E_{NO2-})$, therefore satisfy the following equations:

$$i_{oxdn}(E_{H2O2}) = a1\, i_{H2O2}$$

$$i_{oxdn}(E_{NO}) = a2\, i_{H2O2} + a3\, i_{NO}$$

$$i_{oxdn}(E_{NO2-}) = a4\, i_{H2O2} + a5\, i_{NO} + a6\, i_{NO2-}$$

in which the coefficients a1 to a6 represent calibration constants for the sensors, which can be measured experimentally.

Thus, after carrying out simple subtractions using an electronic circuit, the following is obtained:

$$i_{H2O2} = (1/a1)\, i_{oxdn}(E_{H2O2})$$

$$i_{NO} = (1/a3)\, i_{oxdn}(E_{NO}) - (a2/a1) \cdot (1/a3)\, i_{oxdn}(E_{H2O2})$$

$$i_{NO2-} = (1/a6)\, i_{oxdn}(E_{NO2-}) - (a4/a6)\, i_{H2O2} - (a5/a6)\, i_{NO}$$

At any time t, the instantaneous intensity of the oxidation faradic current, $i_S(t)$, for each chemical species S is proportional to its concentration, $C_S(t)$, in the volume of fluid located above the electrodes which detect it. The proportionality factor depends on a form factor, denoted $\gamma$, which is a function of the geometry of the sensor, and on the Faraday constant, denoted $n_S$, consumed per mole by the chemical species, i.e.:

$$n_{H2O2} = n_{NO2-} = 2 \text{ and } n_{NO} = 1$$

It will be recalled that F denotes the Faraday, i.e. 96 500 Coulombs, the value for the charge carried by one mole of electrons.

The form factor $\gamma$ is a constant imposed by the geometry of the electrochemical device, which can be evaluated theoretically and can be measured experimentally by calibration. For the purposes of simplicity, the three sensors 10A to 100 below will be considered to have identical geometries, and therefore the form factor Y is the same for all of the sensors.

The result is that the concentrations of the chemical species can be obtained from the currents measured by the sensors 10A to 10C, with the aid of the following expressions, in which the temporal variable t has been defined:

$$C_{H2O2}(t) = i_{oxdn}(E_{H2O2}, t)/(2F\gamma)$$

$$C_{NO}(t) = [i_{oxdn}(E_{NO}, t) - i_{oxdn}(E_{H2O2}, t)]/(F\gamma)$$

$$C_{NO2-}(t) = [i_{oxdn}(E_{NO2-}, t) - i_{oxdn}(E_{NO}, t)]/(2F\gamma)$$

In Example 1, the three sensors 10A to 10C can therefore operate in parallel, each with a constant oxidation potential, namely $E_{H2O2}$, $E_{NO}$, and $E_{NO2-}$ respectively.

In accordance with one variational embodiment, only NO and $NO_2^-$ are detected. This embodiment is particularly advantageous when the measurement of $H_2O_2$ is not significant and dose not influence the results of the intended objective. The concentration $C_{H2O2}(t)$ presented above is then considered to be uniformly zero, i.e. $C_{H2O2}(t)=0$. The series of equations is therefore simplified.

Example 2

In Example 2, a single fluidic circuit 9 and a single sensor 10A are used; the others can be dispensed with.

In this case, the sensor 10A operates sequentially in order to detect the chemical species mentioned above during the three successive steps. The oxidation potential is therefore switched between three constant potential stages, respectively equal to the three oxidation potentials mentioned above, for example periodically in accordance with the sequence $E_{H2O2} \rightarrow E_{NO} \rightarrow E_{NO2-} \rightarrow E_{H2O2} \rightarrow E_{NO} \rightarrow E_{NO2-} \rightarrow$ etc.

In this case, each oxidation potential is maintained for a duration that is very long compared with the time constant for the working electrode, this time constant being, for example, a few milliseconds for the microelectrodes employed in the microfluidic channels, and measurements of the current are carried out at the end of each constant potential stage.

The remaining measurement signals can be processed using the same equations as in Example 1.

Example 3

Because nitric oxide is a small molecule that is both hydrophilic and lipophilic, it can easily pass through thin layers of organic polymer, in contrast to the other two species $H_2O_2$ and $NO_2^-$. Thus, it can be detected in isolation with the aid of an electrochemical sensor protected by a filtration layer of this type, for example with a working electrode produced from platinized platinum covered with a thin layer of eugenol (4-allyl-2-methoxyphenol) deposited by electropolymerization.

In Example 3, the sensor 10D is therefore protected by the filtering layer which is schematically represented by the numeral 19. The instantaneous concentration of nitric oxide can therefore be measured independently of that of the chemical species $H_2O_2$ and $NO_2^-$, in accordance with the expression:

$$C_{NO}(t) = [i_{oxdn}(E_{NO}, t)]_{eugenol}/(F\gamma).$$

in which $[i_{oxdn}(E_{NO}, t)]_{eugenol}$ designates the currents measured by the sensor 10D.

The other sensors 10A to 10C and the other fluidic circuits 9 can be dispensed with. This method can therefore advantageously be used with a single sensor when only the concentration of NO is desired.

In a variation, the filter 19 may be disposed in other positions between the collecting element 5 and the sensor 10D. The function of the filter 19 is to filter the sweat in order to prevent certain elements contained therein from perturbing the measurement of NO dissolved in the sweat. Examples of perturbing elements are peroxynitrite (ONOO—) or hydrogen peroxide ($H_2O_2$).

Example 4

In this case, the sensor 10D of Example 3 is merged with the sensors 10A to 10C of Example 1 or with the sensor 10A of Example 2. This configuration can be used to obtain two measurements that are independent of the concentration of dissolved nitric oxide, and thus to check the consistency of the measurements, in particular by verifying that the sensors do not drift, for example linked to partial deactivation of the surface of one of the electrodes.

In this case, the electrochemical electronic control device 40 (FIG. 9) is preferably configured to compare the two measurements of the concentration of nitric oxide and to issue an alarm when the result of the comparison satisfies a predefined criterion, for example if it exceeds a predefined threshold.

In Examples 1 to 4 above, the measured instantaneous faradic currents can be used to measure the concentration of chemical species in the analyzed solution. As a consequence, in a static system, the current intensity is sufficient to bear witness to the production of the detected species.

However, when the detection apparatus 1 is applied to an essentially dynamic physiological system, it is also desirable to be able to access the quantitative dynamics for the production of each chemical species by the cardiovascular system, for example during exertion tests or during medical monitoring. Under dynamic conditions, in order to access the instantaneous quantity of a chemical species, denoted $\Delta Q(t)$, produced over a short period of time, denoted $\Delta t(t)$, it is desirable to know the mean concentration, $C_S(t)$, of the chemical species and the volumetric flow rate of the analyzed fluid simultaneously, namely:

$$d(t)=(\Delta V/\Delta t)$$

in which $\Delta V$ designates the volume scanned during the time interval $\Delta t$. Thus, the intensity of the production flow, denoted $P_S(t)$, of a chemical species S at a time t is given by:

$$P_S(t)=[\Delta Q/\Delta t](t)=C_S(t)\cdot d(t)$$

in which the mean concentration $C_S(t)$ is obtained from the mean intensities of the electrochemical oxidation currents measured between the times t and t+$\Delta t$.

In the context of the envisaged dynamic applications, it is therefore desirable for the detection apparatus 1 to measure, at the same time and at each time t required by the desired accuracy for monitoring the physiological state of the patient over time, for example once per minute, the mean intensities, $i_{av}(t)$, of the faradic current linked to the electrochemical oxidation of the chemical species being monitored and the value for the volumetric flow rate $d(t)$ of sweat at time t in the corresponding fluidic circuit.

Figure 7:
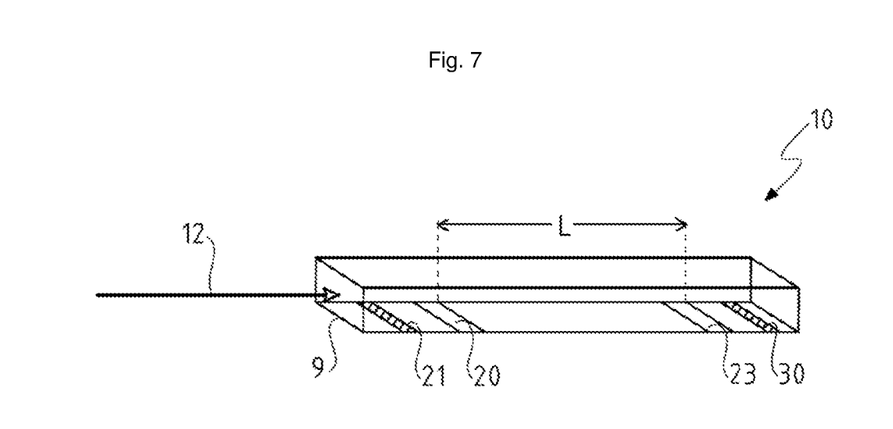
FIG. 7 is a schematic perspective representation of an electrochemical sensor which can be used in the fluidic circuit of FIG. 6.

FIG. 7 illustrates an embodiment of an electrochemical sensor 10 that can meet this dual requirement in an integrated manner. This electrochemical sensor 10 comprises at least one strip microelectrode forming a working electrode 20 or a pair of working electrodes 20, 23. A strip microelectrode of this type may be produced from platinized (platinum black) platinum, which may or may not be covered with a layer of electropolymerized eugenol of micrometric dimensions. A strip microelectrode of this type may be implanted by microfabrication, for example by CVD and/or lithography. This strip microelectrode or these strip microelectrodes can be used to electrochemically oxidize the selected chemical species.

Figure 9:
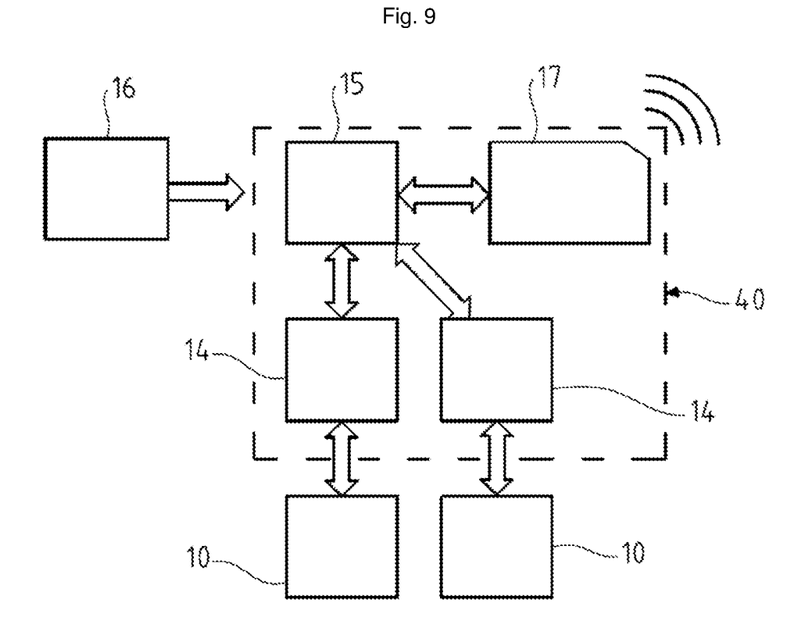
FIG. 9 is a schematic functional representation of a detection device that can be used in the apparatus of FIG. 2.

In addition, the fluidic circuit 9 of FIG. 7 is equipped with a reference electrode 21 that is produced, for example, in the form of an Ag/AgCl microstrip and placed upstream of the working electrode 20 or of the pair of working electrodes 20, 23. Finally, this fluidic circuit 9 is equipped with a counter-electrode 30 produced from platinized platinum placed downstream of the working electrode 20 or of the pair of working electrodes 20, 23. Notwithstanding the functional schematic representation of FIG. 7, the surface of the counter-electrode 30 is in fact two to three times larger than that of the other electrodes.

The entirety of the fluidic circuit 9 with the electrodes 20, 21, 23, 30 is bathed in a lamina of sweat, not shown, and therefore constitutes a microfluidic electrochemical cell with three or four electrodes. Each of the electrodes 20, 21, 23, 30 is connected to an electrochemical electronic control device 40 (FIG. 9) by means of the insulated electrical contacts of the collecting element 5 and the sweat.

This embodiment of an electrochemical sensor 10 may be employed in one or more of the aforementioned fluidic circuits 9.

In order to measure the volumetric flow rate $d(t)$, the electrochemical sensor 10 has to include the pair of working electrodes 20, 23. The solution described here is simple and readily industrializable, because it has no moving parts and it makes no claims to be hydrodynamic. It does not require any interventions aimed at modulating the flow rate of fluid, but is suitable for any reasonable physiological flow rate.

The two working electrodes 20, 23, for example two strips of platinized platinum, may act as working microelectrodes, are electrically independent and are spaced apart by a distance L along the path of the fluid analyzed in the fluidic circuit 9. The two working electrodes 20 and 23 are, for example, installed on the bottom of a linear channel the section of which has a constant area A.

Figure 8:
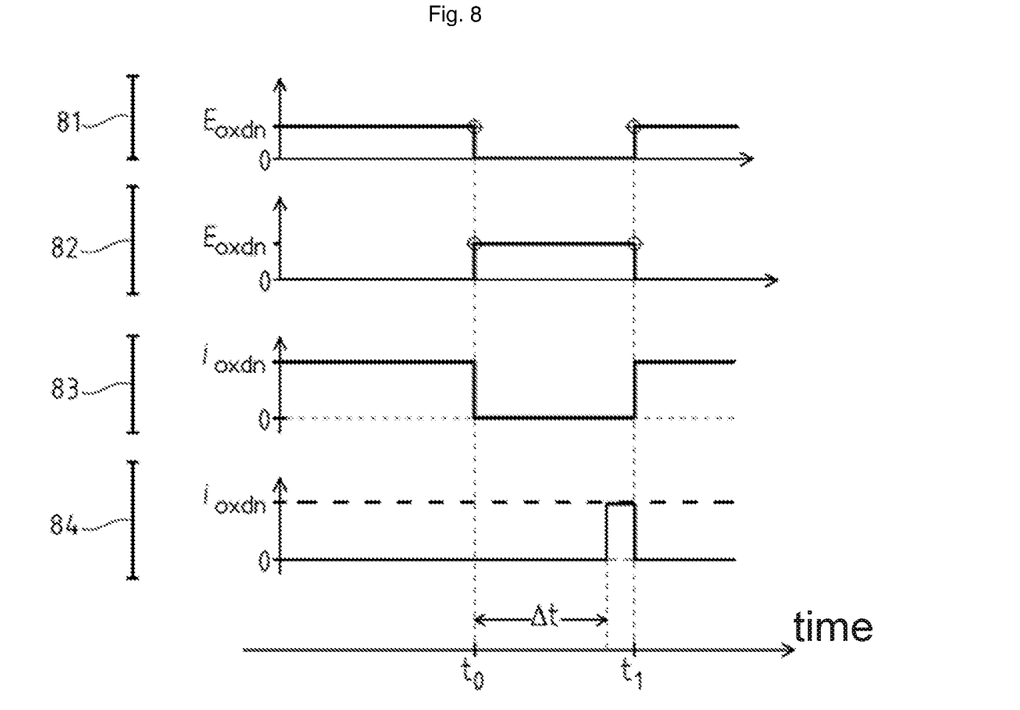
FIG. 8 is a time chart illustrating a detection method that can be used with the electrochemical sensor of FIG. 7.

The working electrode 23 that is positioned downstream is used in accordance with the method illustrated in FIG. 8, which comprises two steps. The plot 81 represents the electric potential applied to the working electrode 20 as a function of time. The plot 82 represents the electrical potential applied to the working electrode 23 as a function of time. The potentials indicated as "0" on plots 81 and 82 in fact signify disconnection of the corresponding electrode (open circuit). The plot 83 represents the faradic current measured at the working electrode 20 as a function of time. The plot 84 represents the faradic current measured at the working electrode 23 as a function of time.

During a first step carried out over a range of time prior to the time $t_0$, the potential $E_{oxdn}$ applied to the working electrode 20 is sufficient to allow oxidation of the target chemical species, while the downstream working electrode 23 is disconnected. The working electrode 20 positioned upstream can then be used to continuously record the instantaneous electrochemical current, $i_{oxdn}(t)$ which, following any calculations as above which might be required, then indicates the concentration $C(t)$ of the target chemical species in the analyzed fluid.

During a second step carried out over a range of time from the time t0, the working electrode 20 is disconnected and the potential $E_{oxdn}$ is applied to the downstream working electrode 23.

At time $t_0$, the flow of sweat passing above the working electrode 23 has already been electrolyzed (completely or partially) during its passage above the working electrode 20 which is located upstream, in a manner such that the concentration of the target chemical species is zero there, or at least much lower than before it enters the electrochemical device. The current intensity $i_{oxdn}$ detected by the working electrode 23 (plot 84) is therefore zero (or at least much lower than that of the current $i_{oxdn}$ detected at the working electrode 20 before the time to).

At the time $t_0+\Delta t$, the working electrode 23 starts to analyze a non-electrolyzed solution and the current intensity $i_{oxdn}$ that it detects becomes of the same order as that detected by the working electrode 20 before the time $t_0$. The growth of current, schematized by a step in FIG. 8, is detected by an ad hoc electronic circuit. The duration $\Delta t$, which is the delay between this growth and the moment t0 of disconnection of the working electrode 20, represents the time necessary for the flow of sweat to transit between the two working electrodes 20 and 23. The duration Δt is represented by a double headed arrow at the bottom of FIG. 8. In order to simplify the representation, it is assumed in FIG. 8 that electrolysis of the target chemical species is complete when the working electrode 20 is connected. The same measurement principles are applicable when this electrolysis is only partial.

The flow velocity v(t) and the rate d(t) can therefore be estimated as follows:

$$v(t)=L/\Delta t$$

$$d(t)=A \cdot v(t)$$

The potential $E_{oxdn}$ applied to the working electrode 23 is sufficient to enable oxidation of the target chemical species, while the working electrode 20 is disconnected. The measurement of concentration may therefore optionally be continued for a certain period with the working electrode 23. The second step ends with the disconnection of the working electrode 23 at the time $t_1$. The working electrode 20 may then be reconnected and the method can be repeated as many times as is necessary in order to evaluate the rate d(t) at successive times.

The distance L between the two working electrodes 20 and 23 is preferably sufficiently small, for example of the order of 1 mm, for the changes in the physiological response of the patient to be negligible over the period Δt.

The method for measuring the rate described above may be employed simultaneously in all of the parallel fluidic circuits. However, if these circuits are configured and supplied in a similar manner, a single measurement of the rate may be sufficient. In this case, the rate measurement method described above may be employed in a single fluidic circuit 9. Furthermore, this rate measurement method can be combined with the sensors from the various Examples 1 to 4 described above.

The methods for detecting concentration and rate described above may be carried out in an automated manner with the aid of an electronic control device 40, which is preferably integrated into the detection apparatus 1.

With reference to FIG. 9, an embodiment of an electronic control device 40 which can be integrated into the detection apparatus 1, for example in the form of an electronic circuit board 13 as shown in FIG. 3, will now be described.

The or each electrochemical sensor 10 is connected to an analog-to-digital converter 14, which in turn supplies a processor 15. The processor 15 is, for example, programmed to execute the methods for detecting the concentration and rate described above.

A source of energy 16, for example a battery, supplies the electronic control device 40. A communication module 17, which may be wired or wireless, may also be provided in order to communicate the results of the measurements of concentration, rate and/or flow of the quantity of material, for one or each target chemical species, to a storage or post-processing device.

Figure 10:
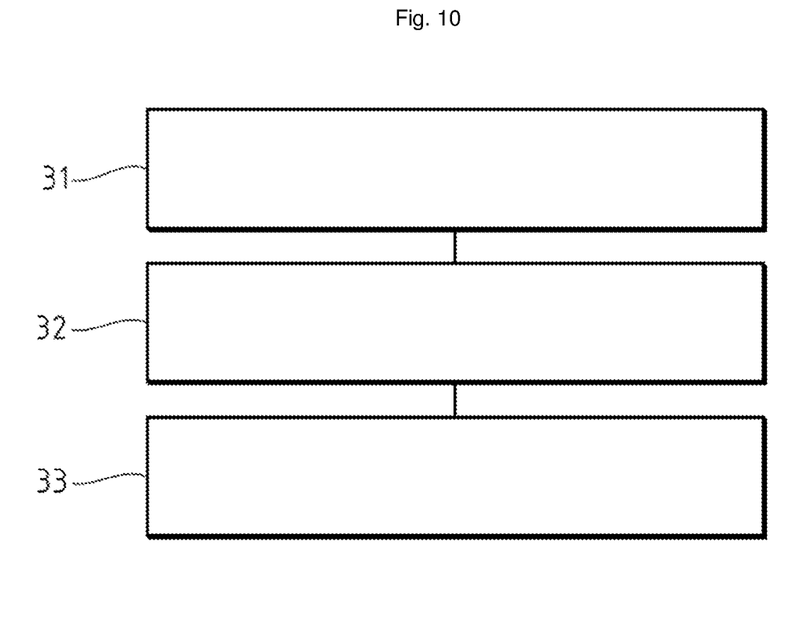
FIG. 10 is a diagram illustrating the steps of a method that can be carried out with the apparatus of FIG. 2.

FIG. 10 represents a method that may be executed by the processor 15 in one embodiment.

In step 31, the instantaneous concentration Cs(t) of a chemical species S is determined from electrochemical measurements.

In step 32, the volumetric rate d(t) in the corresponding fluidic circuit is determined.

In step 33, the flow of the quantity of material for the chemical species under consideration is determined on the basis of Cs(t) and d(t), for example:

$$P_S(t)=C_S(t) \cdot d(t)$$

Figure 11:
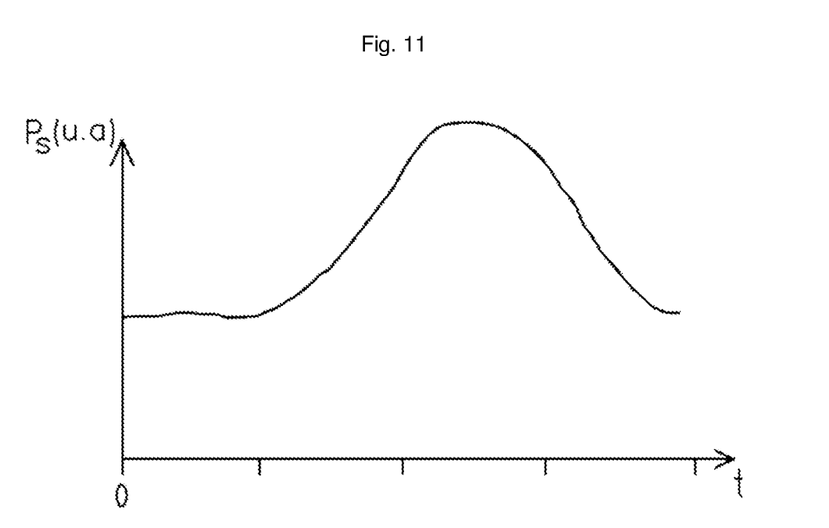
FIG. 11 is a graph illustrating a result of the measurements that can be obtained with the apparatus of FIG. 2.

FIG. 11 is a graph illustrating a measurement signal for the material flow as a function of time that may be obtained with the detection apparatus 1, for example during an exertion test carried out on a subject for the species NO.

The electronic control device 40 optionally comprises other functional modules, for example a gyroscopic module and/or an accelerometer module for detecting the orientation and movements of the subject as well as the level of activity of the subject, and a temperature sensor in order to measure the temperature of the subject's epidermis. It is useful to know the temperature of the skin for the purposes of correlations between temperature and dilation of the vessels.

Certain elements of the detection apparatus 1, in particular the electronic control device 40, may be produced in different forms, in a unitary or distributed manner, using physical and/or software components. Physical components that may be used are application-specific integrated circuits, ASIC, field programmable gate arrays, FPGA, or microprocessors. The software components may be written in various programming languages, for example C, C++, Java or VHDL. This list is not exhaustive.

Although the invention has been described in connection with several particular embodiments, it is clear that it is not in any way limited to them and it encompasses all equivalent techniques for the means described as well as their combinations if they fall within the scope of the invention.

The use of the verb "compose", "comprise" or "include" and their conjugated forms does not exclude the presence of elements or other steps other than those defined in a claim.

In the claims, none of the reference signs in parentheses should be interpreted as limiting the claim.

The invention claimed is:

1. A detection apparatus (1) for detecting at least one chemical species dissolved in the sweat of a human or animal subject, said at least one dissolved chemical species including nitric oxide NO, said apparatus comprising:
   a collecting element (5) intended to be placed on an investigation zone of a subject's epidermis (2),
   a detection device comprising at least one fluidic circuit (8, 9) coupled to the collecting element in order to conduct at least one flow of sweat originating from the investigation zone, and at least one electrochemical sensor (10) comprising electrodes disposed in the at least one fluidic circuit, in which said electrodes comprise at least one working electrode (20) and a counter-electrode (30), the at least one electrochemical sensor being configured to produce at least a signal that is representative of a concentration of nitric oxide NO in the flow of sweat by an electrical measurement between the at least one working electrode and the counter-electrode,
   wherein said electrodes further comprise an upstream working electrode (20) and a downstream working electrode (23) spaced apart in the at least one fluidic circuit in a direction of flow (12) of the flow of sweat, and the at least one electrochemical sensor being configured to produce a signal that is representative of a flow velocity of the flow of sweat by measuring a delay (Δt) between a variation in current in the upstream working electrode and a variation in current in the downstream working electrode.

2. The apparatus as claimed in claim 1, in which the detection device is configured to produce a signal that is representative of an instantaneous production of nitric oxide NO in the investigation zone on the basis of a signal that is representative of the concentration of nitric oxide NO and of a signal that is representative of the flow velocity of the flow of sweat.

3. The apparatus as claimed in claim 1, in which the at least one electrochemical sensor is configured to produce the signal that is representative of the concentration of the nitric oxide NO by an amperometric measurement between the at least one working electrode and the counter-electrode.

4. The apparatus as claimed in claim 1, in which said at least one chemical species additionally includes the nitrite ion $NO_2^-$ and/or hydrogen peroxide $H_2O_2$.

5. The apparatus as claimed in claim 4, in which the at least one electrochemical sensor (10A) is configured for the sequential detection of several chemical species during a plurality of measurement steps, the at least one electrochemical sensor being configured to polarize the electrodes to an electrical potential for the oxidation of hydrogen peroxide $H_2O_2$ during a first step and to polarize the electrodes to an electrical potential for the oxidation of nitric oxide NO during a second step, and in which the detection device is configured to produce the signal that is representative of a concentration of nitric oxide NO on the basis of a first amperometric measurement signal obtained during the first step and of a second amperometric measurement signal obtained during the second step.

6. The apparatus as claimed in claim 4, in which the detection device comprises:
a first fluidic circuit (9) coupled to the collecting element in order to conduct a first flow of sweat originating from the investigation zone and a first electrochemical sensor (10A) comprising electrodes disposed in the first fluidic circuit, the first electrochemical sensor being configured to polarize the electrodes to an electrical potential for the oxidation of hydrogen peroxide $H_2O_2$, and
a second fluidic circuit (9) coupled to the collecting element in order to conduct a second flow of sweat originating from the investigation zone and a second electrochemical sensor (10B) comprising electrodes disposed in the second fluidic circuit, the second electrochemical sensor being configured to polarize the electrodes to an electrical potential for the oxidation of nitric oxide NO,
in which the detection device is configured to produce a signal that is representative of a concentration of nitric oxide NO on the basis of a first amperometric measurement signal produced by the first electrochemical sensor (10A) and of a second amperometric measurement signal produced by the second electrochemical sensor (10B).

7. The apparatus as claimed in claim 6, in which the detection device (5, 6) additionally comprises:
a third fluidic circuit (9) coupled to the collecting element in order to conduct a third flow of sweat originating from the investigation zone and a third electrochemical sensor (10C) comprising electrodes disposed in the third fluidic circuit, the third electrochemical sensor being configured to polarize the electrodes to an electrical potential for the oxidation of the nitrite ion $NO_2^-$, and in which the detection device is configured to produce a signal that is representative of a concentration of the nitrite ion $NO_2^-$ on the basis of said first and second amperometric measurement signals and of a third amperometric measurement signal produced by the third electrochemical sensor.

8. The apparatus as claimed in claim 6, in which the detection device additionally comprises:
a fourth fluidic circuit (9) coupled to the collecting element in order to conduct a fourth flow of sweat originating from the investigation zone, and a fourth electrochemical sensor (10D) comprising electrodes disposed in the fourth fluidic circuit, in which the fourth electrochemical sensor is configured to polarize the electrodes to an electrical potential for the oxidation of nitric oxide NO and in which the fourth fluidic circuit comprises a filter (19) that is configured to filter the flow of sweat reaching the fourth electrochemical sensor in order to eliminate hydrogen peroxide $H_2O_2$.

9. The apparatus as claimed in claim 8, in which the detection device is configured to compare a measurement of the concentration of nitric oxide obtained with the fourth electrochemical sensor (10D) with a measurement of the concentration of nitric oxide obtained with the first and second electrochemical sensors (10A, 10B) and to issue an alarm when the result of the comparison satisfies a predefined criterion.

10. The apparatus as claimed in claim 1, in which the collecting element (5) comprises a fibrous body for conducting the sweat by capillary action.

11. The apparatus as claimed in claim 1, additionally comprising an envelope (7) surrounding the collecting element (5) in a manner such as to form an impervious barrier around the investigation zone by contact with the epidermis (2) of said subject.

12. The apparatus as claimed in claim 1, additionally comprising a wired or wireless communication device (17) configured to transmit one or more measurement signals produced by the detection device to a storage or post-processing device.

13. The apparatus as claimed in claim 1, in which the at least one fluidic circuit (9) is formed in an insulating support (6) and in which the electrodes of the at least one electrochemical sensor (10) are constituted by metallic deposits on said insulating support, the metallic deposits being selected from the group consisting of silver, gold, platinum and platinum black.

14. The apparatus as claimed in claim 1, additionally comprising a gyroscopic module and/or at least one accelerometer for detecting a state of activity of the subject.

15. The apparatus as claimed in claim 1, additionally comprising a temperature sensor for measuring the temperature of the epidermis of the subject.

16. A method for determining the production ($P_S$) of at least one chemical species by a human or animal subject, said at least one chemical including nitric oxide NO, the method comprising:
selecting an investigation zone of an epidermis of said subject,
applying an apparatus (1) as claimed in claim 1 for a duration that is necessary for the production of the signal which is representative of a concentration of nitric oxide NO in the flow of sweat and the signal that is representative of a flow velocity of the flow of sweat, and
determining a measurement of the production ($P_S$) of nitric oxide NO by the subject from a signal that is representative of the concentration of nitric oxide NO in the flow of sweat and of a signal that is representative of the flow velocity of the flow of sweat.

17. The method as claimed in claim 16, additionally comprising:
evaluating distress in the vascular tissues of the subject from the measurement of the production of nitric oxide NO.

18. The method as claimed in claim 16, additionally comprising:
evaluating a cardiovascular capacity of the subject from the measurement of the production of nitric oxide NO.

19. A detection apparatus (1) for detecting at least one chemical species dissolved in the sweat of a human or animal subject, said at least one dissolved chemical species including nitric oxide NO, said apparatus comprising:
a collecting element (5) intended to be placed on an investigation zone of a subject's epidermis (2), and
a detection device comprising at least one fluidic circuit (8, 9) coupled to the collecting element in order to conduct at least one flow of sweat originating from the investigation zone, and at least one electrochemical sensor (10) comprising electrodes disposed in the at least one fluidic circuit, the at least one electrochemical sensor being configured to produce at least a signal that is representative of a concentration of nitric oxide NO in the flow of sweat and a signal that is representative of a flow velocity of the flow of sweat, in which the at least one electrochemical sensor (10D) is configured to polarize the electrodes to an electrical potential for the oxidation of nitric oxide NO and in which the detection device comprises a filter (19) that is configured to filter the flow of sweat reaching the at least one electrochemical sensor in order to eliminate hydrogen peroxide.

20. The apparatus as claimed in 19, wherein the filter (19) comprises a layer of eugenol (4-allyl-2methoxyphenol) deposited on at least one electrode of the electrochemical sensor (10D).

21. A detection apparatus (1) for detecting at least one chemical species dissolved in the sweat of a human or animal subject, said at least one dissolved chemical species including nitric oxide NO, said apparatus comprising:
a collecting element (5) intended to be placed on an investigation zone of a subject's epidermis (2), and
a detection device comprising at least one fluidic circuit (8, 9) coupled to the collecting element in order to conduct at least one flow of sweat originating from the investigation zone, and at least one electrochemical sensor (10) comprising electrodes disposed in the at least one fluidic circuit, the at least one electrochemical sensor being configured to produce at least a signal that is representative of a concentration of nitric oxide NO in the flow of sweat and a signal that is representative of a flow velocity of the flow of sweat, in which said at least one chemical species additionally includes the hydrogen peroxide $H_2O_2$, in which the at least one electrochemical sensor (10A) is configured for the sequential detection of several chemical species during a plurality of measurement steps, the at least one electrochemical sensor being configured to polarize the electrodes to an electrical potential for the oxidation of hydrogen peroxide $H_2O_2$ during a first step and to polarize the electrodes to an electrical potential for the oxidation of nitric oxide NO during a second step, and in which the detection device is configured to produce the signal that is representative of a concentration of nitric oxide NO on the basis of a first amperometric measurement signal obtained during the first step and of a second amperometric measurement signal obtained during the second step.

22. The apparatus as claimed in claim 21, wherein the electrochemical sensor (10A) is configured to polarize the electrodes to an electrical potential for the oxidation of the nitrite ion $NO_2-$ during a third step, and in which the detection device is configured to produce a signal that is representative of a concentration of the nitrite ion $NO_2-$ on the basis of said first and second amperometric measurement signals and of a third amperometric measurement signal obtained during the third step.

* * * * *